United States Patent
Sobotta et al.

(10) Patent No.: US 7,285,672 B2
(45) Date of Patent: Oct. 23, 2007

(54) PROCESS FOR ISOLATING OF α-MANGOSTIN

(75) Inventors: Rainer Sobotta, Ingelheim (DE); Hans-Peter Ignatow, Ingelheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 11/181,289

(22) Filed: Jul. 14, 2005

(65) Prior Publication Data

US 2006/0014967 A1 Jan. 19, 2006

(30) Foreign Application Priority Data

Jul. 17, 2004 (DE) .................. 10 2004 034 683

(51) Int. Cl.
*C07D 311/82* (2006.01)
(52) U.S. Cl. ..................................... 549/393
(58) Field of Classification Search ................. 549/393
See application file for complete search history.

(56) References Cited

FOREIGN PATENT DOCUMENTS

JP 2002047180 * 2/2002

OTHER PUBLICATIONS

Jefferson et al., Australian Journal of Chemistry, "Studies in the xanthone series", 1970, vol. 23, pp. 2539-2543.*
Govindachari et al., Tetrahedron, "Xanthones of *Garcinia mangostana* linn", 1971, vol. 27, pp. 3919-3926.*
English translation of JP 2002-47180, Aug. 8, 2006.*
Sakai, et al; The Structure of Garcinone E; Chem. Pharm. Bull.; vol. 45; No. 5; 1993 Pharmaceutical Society of Japan; pp. 958-960.
Chen; et al; Active Constituents Against HIV-1 Protease from Garcinia mangostana; Planta Medica; vol. 62; 1996; pp. 381-382.
Linuma, et al; Antibacterial Activity of Xanthones from Guttiferaeous Plants against Methicillin-resistant Staphylococcus aureus; J. Pharmacol.; vol. 48; 1996; pp. 861-865.
Yates, et al; the Structure of Magostin; Journal of American Chemical Society; 1958; vol. 80; pp. 1691-1700.
Gopalakrishnan, et al; Evaluation of the Antifungal Activity of Natural Xanthones from Garcinia mangostana and Their Synthetic Derivatives; J. Nat. Prod. 1997; vol. 60; pp. 519-524.

* cited by examiner

*Primary Examiner*—Margaret D. Seaman
*Assistant Examiner*—Niloofar Rahmani
(74) *Attorney, Agent, or Firm*—Michael P. Morris; Mary-Ellen M. Devlin; Philip I. Datlow

(57) ABSTRACT

The invention relates to a process for obtaining and purifying pure α-mangostin from the rind of the fruit (mangosteen) of *Garcinia mangostana*.

27 Claims, No Drawings

PROCESS FOR ISOLATING OF α-MANGOSTIN

BACKGROUND TO THE INVENTION

The invention relates to a process for obtaining and purifying pure α-mangostin from the rind of the fruit ("mangosteen") of *Garcinia mangostana*. The mangosteen is the fruit of the *Garcinia mangostana* tree which originates from the Malaysian Archipelago, is widespread throughout the tropics and grows up to 15 m tall.

The fruits, which are roughly the size of a mandarin to an orange and are dark violet to brownish purple in colour, are highly prized on account of the intensely sweet acidic flavour of their flesh. The juice and the 8 mm thick, tough, leathery rind of the fruit have been shown to contain, among other things, the yellow xanthone derivatives α-mangostin and γ-mangostin. α-Mangostin is 1,3,6-trihydroxy-7-methoxy-2,8-bis-(3-methyl-but-2-enyl)-xanthen-9-one of formula 1, while γ-mangostin is the alcohol thereof which is free in the 7 position.

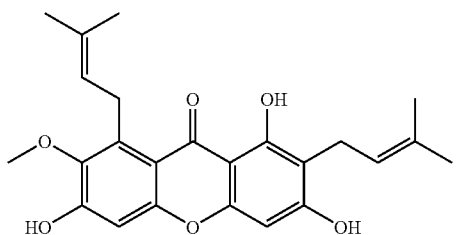

1

In the literature α-mangostin is described as a substance with an antihistamine and antiserotonin activity. Nowadays it is also used in the cosmetics industry. There is consequently a great demand for the pure compound.

Various suggestions for methods of purifying and isolating α-mangostin can be found in the literature. Thus, back in 1958, Yates et al. (J. Am. Chem. Soc. (1958) 80, 1691) dislcosed extraction of the fruit rinds to recover mangostin from *Garcinia mangostana*. However, this process, as in all subsequent publications, required chromatographic separation to isolate the α-mangostin after the plant material had been extracted, (Sakai et al. Chem. Pharm. Bull (1993) 41, 958; Govindachari et al. Tetrahedron (1971), 27, 3919; Gopalakrishnan et al. J. Nat. Prod. (1997) 60, 519, Chen et al. Planta Med. (1996) 62, 381; Iinuma et al. J. Pharm. Pharmacol. (1996) 48, 861)

The increasing demand for α-mangostin cannot be met by these methods. The aim of the present invention was therefore to provide a quick and simple method of isolating and purifying α-mangostin. Preferably, this process should be suitable for use on an industrial scale.

DETAIL DESCRIPTION OF THE INVENTION

Surprisingly it has now been found that highly pure α-mangostin can be obtained from an extract of ground mangosteen rinds if this extract is subjected to further distribution between toluene and a diol.

The present invention is thus based on a process for obtaining α-mangostin from ground mangosteen rinds, in which the following steps are carried out one after another
a) extraction of the plant material with an extraction solvent consisting of an aromatic solvent;
b) concentrating and crystallising from an aromatic solvent;
c) dissolving the crude product in a diol and optionally toluene;
d) distributing the dissolved crude product between toluene and a diol;
e) concentrating the aromatic phase and recrystallising from alcohol/water.

Preferably in step a) of the above process the extraction solvent is toluene.

Preferably in step a) of the above process the extraction takes place at 40–100° C., preferably 50–90° C., most preferably 59–71° C.

Preferably in step b) of the above process crystallisation is carried out using toluene.

Preferably in step c) of the above process the dissolving is carried out using a mixture of a diol and toluene in a ratio of 90:1 to 99:1, preferably 93:7 to 98:2, more preferably 95:5 to 97:3, most preferably about 96:4.

Preferably in step c) of the above process the diol is 1,2-ethanediol, 1,2-propanediol, 1,3-propanediol, 1,2-, 1,3- or 1,4-butanediol, most preferably 1,2-ethanediol.

Preferably in step c) of the above process the dissolving of the crude product is carried out at 60–100° C., preferably 70–90°, most preferably 80° C.

Preferably in step d) of the above process the distribution is carried out in countercurrent in a Kühni column.

Preferably, in step d) of the above process, the diol is 1,2-ethanediol, 1,2-propanediol, 1,3-propanediol, 1,2-, 1,3- or 1,4-butanediol, most preferably 1,2-ethanediol.

Preferably in step d) of the above process, the distribution is carried out at 10–35° C., preferably 15-30°, most preferably 20–25° C.

Preferably in step e) of the above process, the recrystallisation is carried out using ethanol/water.

Particularly preferably in the above process the plant material is pre-softened in water for 5–20 hours, preferably 10–15 hours, most preferably 12–13 hours, before the extraction in step a) and is then combined with two to four times, preferably three times the amount of toluene. Most preferably the toluene is at a temperature of 40–90° C., preferably 50–80° C., most preferably 60–70° C.

Particularly preferred, therefore, is a process for obtaining α-mangostin from ground mangosteen rinds in which the following steps are carried out in succession:
Combining plant material pre-softened in water with toluene at a temperature of 40–90° C.;
Extraction at 40–100° C. with an extraction solvent consisting of toluene;
Concentration and crystallisation from toluene;
Dissolving the crude product in a mixture of 1,2-ethanediol and toluene in a ratio of 93:7 to 98:2 at 60–100° C.;
Distributing the dissolved crude product between toluene and 1,2-ethanediol at 10–35° C.;
Concentration and recrystallisation from ethanol/water.

Thus, most preferred is a process for obtaining α-mangostin from ground mangosteen rinds in which the following steps are carried out in succession:
Combining plant material which has been pre-softened in water with toluene warmed to 60–70° C.;
Extraction at 59–71° C. with toluene;
Concentration and recrystallisation from toluene;
Dissolving the crude product in a mixture of 1,2-ethanediol and toluene in a ratio of about 96:4 at 80° C.;
Cooling to RT and filtering the solution;
Distributing in a Kühni column in countercurrent with toluene at 20–25° C.;

Concentrating the mixture down to a stirrable suspension;

Cooling to 10–15° C. and suction filtering;

Recrystallising from ethanol/water.

Terms and Definitions Used

By a "Kühni column" is meant within the scope of the invention a column in which one solvent 1 is added from above, with stirring, and at the same time another solvent 2 is introduced into the column from below. The solvent 2 has a lower density than the solvent 1. If the two solvents are immiscible with each other, a continuous distribution process can be carried out in this way. This type of column for liquid-liquid distribution is known in the prior art.

By an "aromatic solvent" is meant within the scope of the present invention a solvent or solvent mixture selected from among benzene, toluene, o-xylene, m-xylene, p-xylene and mesitylene.

By an "alcohol" is meant according to the invention a branched or unbranched alkyl group having 1 to 6 carbon atoms and a hydroxyl group. Examples include methanol, ethanol, propanol, butanol and pentanol, including all the isomers and mixtures thereof.

By a "diol" is meant within the scope of the present invention a branched or unbranched alkyl group having 2 to 6 carbon atoms and two hydroxyl groups. Examples include ethanediol, propanediol, butanediol, pentanediol and hexanediol, including all isomers and mixtures thereof.

EXAMPLES

The Examples that follow serve to illustrate the process carried out by way of example in order to obtain α-mangostin. They are to be regarded solely as possible procedures described by way of example without restricting the invention to their contents.

Extraction 600 g of ground mangosteen rinds are combined with 300 g of water, mixed and a left to stand overnight. The mashed ground material is then transferred into the extractor and 1000 ml of warm toluene (60–70° C.) are added. Extraction is carried out with 8260 ml of toluene at a flow rate of 2360–2700 ml/h at 59–71° C. The micelle formed is evaporated down at 70° C. and at 85–100 mbar.

A residue remains consisting of 56.7 g of dark brown viscose oil. 85 ml of toluene are added to the residue and the contents are brought into solution at 70° C. After inoculation the mixture is cooled to RT with stirring and a further 15 ml of toluene are added, after which the mixture is cooled to 10° C. The resulting suspension is suction filtered through a filter and washed with 45 ml of cold toluene. The isolated crude product 1 is dried at 55° C. in vacuo; yield: 29.0 g.

Distribution 1 kg of crude product 1 is dissolved in 12.5 litres of 1,2-ethanediol and 522 ml of toluene at 80° C. and then cooled to RT. The solution is filtered and extracted with toluene at 20–25° C. in countercurrent in a pilot Kühni column. The crude product solution is fed in at the top edge of the mixing zone while toluene is fed in at the lower edge of the mixing zone, with stirring (see Table 1). The toluene extract obtained from the distribution is evaporated down in vacuo until a suspension is obtained which is still stirrable: 2653 g of yellow suspension. The suspension is cooled to 10–15° C. and suction filtered through a filter. The filter residue is washed with 450 ml of cold toluene, suction filtered dry and dried at 55° C. in vacuo. Yield of crude product 2: 526.74 g of yellow crystals.

TABLE 1

Pilot Kühni column distribution

| | | Crude product solution | | Toluene | |
|---|---|---|---|---|---|
| Time [min] | Stirrer Step | Throughflow [ml/min] | Total Throughput [l] | Throughflow [ml/min] | Total Throughput [l] |
| 0 | 8 | | | 485 | 1.00 |
| 5 | 8 | 54.7 | 0.30 | 511 | 4.31 |
| 20 | 6 | 44.0 | 1.12 | 522 | 12.90 |
| 35 | 6.5 | 45.0 | 1.72 | 524 | 19.35 |
| 45 | 5.75 | 46.0 | 2.38 | 522 | 26.76 |
| 65 | 6 | 49.0 | 3.20 | 515 | 35.04 |
| 75 | 5.5 | 58.0 | 3.90 | 614 | 42.40 |
| 105 | 5.5 | 63.0 | 5.67 | 616 | 60.00 |
| 163 | 5.5 | 59.0 | 9.20 | 610 | 95.00 |
| 183 | 5.5 | 76.0 | 10.10 | 766 | 105.00 |
| 210 | 5.5 | 76.0 | 12.50 | 767 | 129.00 |
| 223 | 5.5 | 76.0 | 13.40 | 768 | 138.70 |
| 251 | 5.5 | | 15.70 | 850 | 158.40 |
| 275 | 5.5 | | 17.14 | 850 | 175.20 |

Recrystallisation 500 g of crude product 2 are dissolved in 1400 ml of ethanol at 30–35° C., filtered and the filter is washed with 50 ml of ethanol. 725 ml of water are added to the solution at 30–35° C., with stirring, within 25 min and the mixture is inoculated with pure α-mangostin. The suspension formed is stirred for a further 90 min at 27–30° C. Then at 27–28° C., 725 ml of water are added within 40 min with stirring and the mixture is cooled to 10° C. within 35 min. The suspension is suction filtered through a filter, the filter material is washed with 400 ml of cold ethanol-water mixture (1:1) and dried at 55° C. in vacuo. Yield of α-mangostin: 487.1 g of yellow crystals.

The invention claimed is:

1. A process for obtaining α-mangostin from ground mangosteen rinds, said process comprising carrying out the following steps one after the other:
   a) extracting the plant material with an extraction solvent comprising toluene;
   b) concentrating and crystallizing a crude product from the extraction solvent;

c) dissolving the crude product in a solvent comprising a diol and optionally further comprising toluene;

d) distributing the dissolved crude product between a toluene phase and a diol phase, whereby before distributing, if toluene was not added in step c), toluene is added to the dissolved crude product or, if toluene was added in step c), optionally, further toluene is added to the dissolved crude product;

e) concentrating the toluene phase and, from the concentrate, recrystallising α-mangostin from alcohol/water.

2. The process according to claim 1, wherein in step a) the extraction is carried out at 40–100° C.

3. The process according to claim 1, wherein in step b) crystallization is carried out from toluene.

4. The process according to claim 1, wherein in step c) a mixture of a diol and toluene in a ratio of 90:1 to 99:1 is used as the solvent for the dissolving.

5. The process according to claim 1, wherein in step c) the dissolving of the crude product is carried out at 60–100° C.

6. The process according to claim 1, wherein in step d) the distribution is carried out in countercurrently in a Kühni column.

7. The process according to claim 1, wherein in step d) the distribution is carried out at 10–35° C.

8. The process according to claim 1, wherein in steps c) and d) the diol is 1,2-ethanediol.

9. The process according to claim 1, wherein in step e) the recrystallization is carried out with ethanol/water.

10. The process according to claim 1, wherein the plant material is pre-softened in water for 5–20 hours before step a) and is then combined with three times the amount of toluene at 40–90° C.

11. The process according to claim 2, wherein in step c) a mixture of a diol and toluene in a ratio of 90:1 to 99:1 is used as the solvent for the dissolving.

12. The process according to claim 2, wherein in step c) the dissolving of the crude product is carried out at 60–100° C.

13. The process according to claim 11, wherein in step c) the dissolving of the crude product is carried out at 60–100° C.

14. The process according to claim 7, wherein in step d) the distribution is carried out countercurrently in a Kühni column.

15. The process according to claim 2, wherein in step d) the distribution is carried out at 10–35° C.

16. The process according to claim 4, wherein in step d) the distribution is carried out at 10–35° C.

17. The process according to claim 5, wherein in step d) the distribution is carried out at 10–35° C.

18. The process according to claim 2, wherein in steps c) and d) the diol is 1,2-ethanediol.

19. The process according to claim 4, wherein in steps c) and d) the diol is 1,2-ethanediol.

20. The process according to claim 5, wherein in steps c) and d) the diol is 1,2-ethanediol.

21. The process according to claim 7, wherein in steps c) and d) the diol is 1,2-ethanediol.

22. The process according to claim 2, wherein in step e) the recrystallization is carried out with ethanol/water.

23. The process according to claim 4, wherein in step e) the recrystallization is carried out with ethanol/water.

24. The process according to claim 5, wherein in step e) the recrystallization is carried out with ethanol/water.

25. The process according to claim 7, wherein in step e) the recrystallization is carried out with ethanol/water.

26. The process according to claim 8, wherein in step e) the recrystallization is carried out with ethanol/water.

27. The process according to claim 1, wherein in steps c) and d) the diol is: 1,2-ethanediol; 1,2-propanediol; 1,3-propanediol; 1,2-butanediol; 1,3-butanediol or 1,4-butanediol.

* * * * *